United States Patent
Lee et al.

(10) Patent No.: US 7,033,345 B2
(45) Date of Patent: Apr. 25, 2006

(54) DEFLECTABLE MICROIMPLANT DELIVERY SYSTEM

(75) Inventors: Michael J. Lee, Santa Rosa, CA (US); Kristian P. Kristoffersen, Santa Rosa, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 480 days.

(21) Appl. No.: 10/152,110

(22) Filed: May 21, 2002

(65) Prior Publication Data

US 2004/0039338 A1   Feb. 26, 2004

(51) Int. Cl.
A61M 25/01 (2006.01)
A61M 37/00 (2006.01)
A61M 5/00 (2006.01)

(52) U.S. Cl. ............... 604/528; 604/95.04; 604/263
(58) Field of Classification Search ........ 604/528–523, 604/95.04, 263, 530, 532
See application file for complete search history.

(56) References Cited

U.S. PATENT DOCUMENTS

| | | |
|---|---|---|
| 3,780,733 A | 12/1973 | Martinez-Manzor |
| 4,578,057 A | 3/1986 | Sussman |
| 4,898,577 A | 2/1990 | Badger et al. |
| 5,092,848 A | 3/1992 | deCiutiis |
| 5,281,218 A | 1/1994 | Imran |
| 5,336,252 A | 8/1994 | Cohen |
| 5,354,279 A | 10/1994 | Hofling |
| 5,380,292 A | 1/1995 | Wilson |
| 5,437,632 A | 8/1995 | Engelson |
| 5,591,159 A | 1/1997 | Taheri |
| 5,606,974 A | 3/1997 | Castellano et al. |
| 5,658,263 A | 8/1997 | Dang et al. |
| 5,785,689 A | 7/1998 | de Toledo et al. |
| 5,797,870 A | 8/1998 | March et al. |
| 5,814,028 A | 9/1998 | Swartz et al. |
| 5,876,373 A | 3/1999 | Giba et al. |
| 5,916,214 A | 6/1999 | Cosio et al. |
| 5,921,982 A | 7/1999 | Lesh et al. |
| 5,964,754 A | 10/1999 | Osypka |
| 5,980,545 A | 11/1999 | Pacala et al. |
| 5,989,278 A | 11/1999 | Mueller |
| 6,036,677 A | 3/2000 | Javier, Jr. et al. |
| 6,045,530 A | 4/2000 | Krueger et al. |
| 6,045,565 A | 4/2000 | Ellis et al. |
| 6,066,126 A | 5/2000 | Li et al. |
| 6,093,177 A | 7/2000 | Javier, Jr. et al. |
| 6,106,520 A | 8/2000 | Laufer et al. |

(Continued)

FOREIGN PATENT DOCUMENTS

EP   0861632   9/1998

(Continued)

*Primary Examiner*—Nicholas D. Lucchesi
*Assistant Examiner*—Roz Maiorino
(74) *Attorney, Agent, or Firm*—Blakely, Sokoloff, Taylor & Zafman LLP

(57) ABSTRACT

The present invention provides a deflectable catheter-based system for assisting in the delivery of therapeutic agents, cellular materials and the like to one or more sites in a target body tissue. The system provides for one or more injections to a predetermined needle insertion depth with a single core needle that can be advanced and retracted from the tip of the catheter. The catheter assembly includes a handle subassembly having a mechanism for setting and limiting the depth of insertion of the needle, a slide for moving the injection needle between retracted and extended positions, a return spring for biasing the needle to the retracted position, and a modified pulley mechanism for compensating for catheter shaft compression when the catheter is deflected.

34 Claims, 4 Drawing Sheets

U.S. PATENT DOCUMENTS

| | | | |
|---|---|---|---|
| 6,126,654 A | 10/2000 | Giba et al. | |
| 6,165,164 A | 12/2000 | Hill et al. | |
| 6,165,183 A | 12/2000 | Kuehn et al. | |
| 6,179,809 B1 | 1/2001 | Khairkhahan et al. | |
| 6,183,444 B1 | 2/2001 | Glines et al. | |
| 6,206,893 B1 | 3/2001 | Klein et al. | |
| 6,224,584 B1 | 5/2001 | March et al. | |
| 6,241,710 B1 | 6/2001 | VanTassel et al. | |
| 6,251,104 B1 | 6/2001 | Kesten et al. | |
| 6,269,819 B1 | 8/2001 | Oz et al. | |
| 6,270,496 B1 | 8/2001 | Bowe et al. | |
| 6,283,947 B1 | 9/2001 | Mirzaee | |
| 6,309,370 B1 | 10/2001 | Haim et al. | |
| 6,312,447 B1 | 11/2001 | Grimes | |
| 6,322,548 B1 | 11/2001 | Payne et al. | |
| 6,358,258 B1 | 3/2002 | Arcia et al. | |
| 6,511,471 B1* | 1/2003 | Rosenman et al. | 604/528 |
| 6,554,794 B1* | 4/2003 | Mueller et al. | 604/95.04 |
| 6,599,267 B1 | 7/2003 | Ray et al. | |
| 6,623,473 B1* | 9/2003 | Ponzi | 604/528 |
| 2001/0023349 A1 | 9/2001 | VanTassel et al. | |
| 2002/0035361 A1 | 3/2002 | Houser et al. | |
| 2003/0181869 A1* | 9/2003 | Swenson et al. | 604/263 |
| 2003/0220619 A1* | 11/2003 | Polidoro et al. | 604/263 |

FOREIGN PATENT DOCUMENTS

| | | |
|---|---|---|
| EP | 0938871 | 9/1999 |
| WO | WO 92/10142 | 6/1992 |
| WO | WO 00/71196 | 11/2000 |
| WO | WO 01/45548 | 6/2001 |
| WO | WO 01/49357 | 7/2001 |

\* cited by examiner

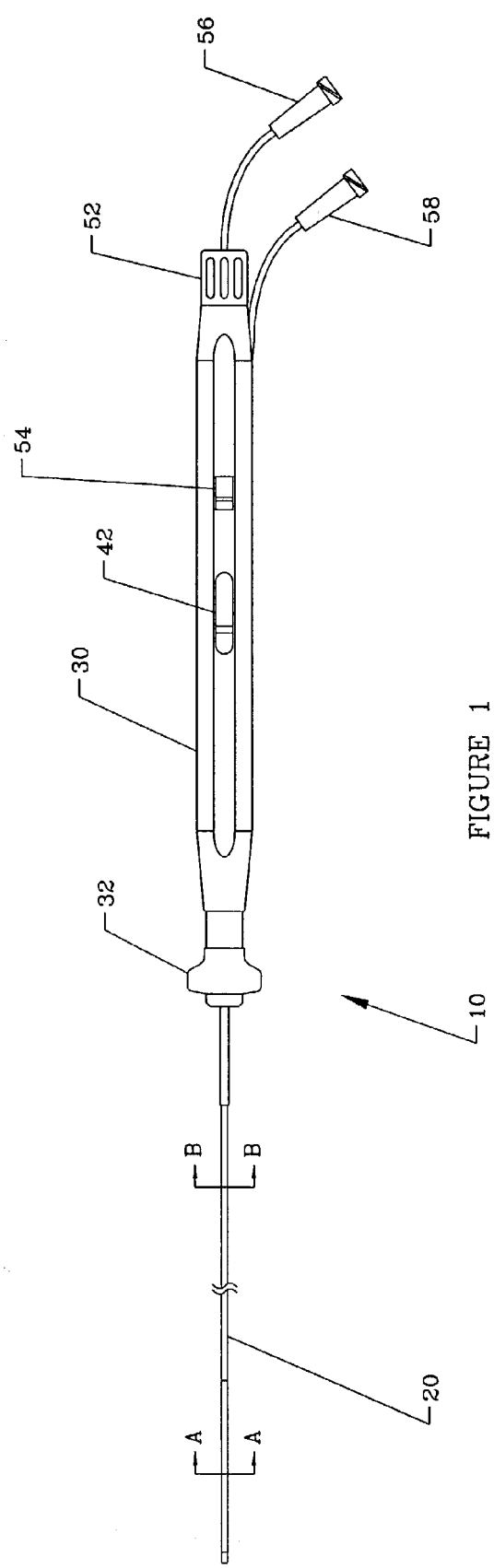
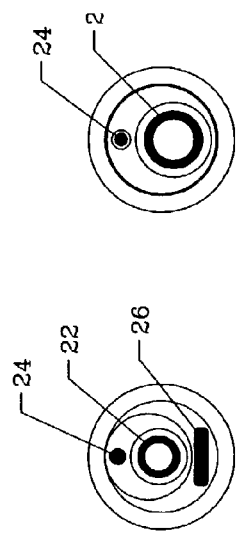
FIGURE 1
FIGURE 1A
FIGURE 1B

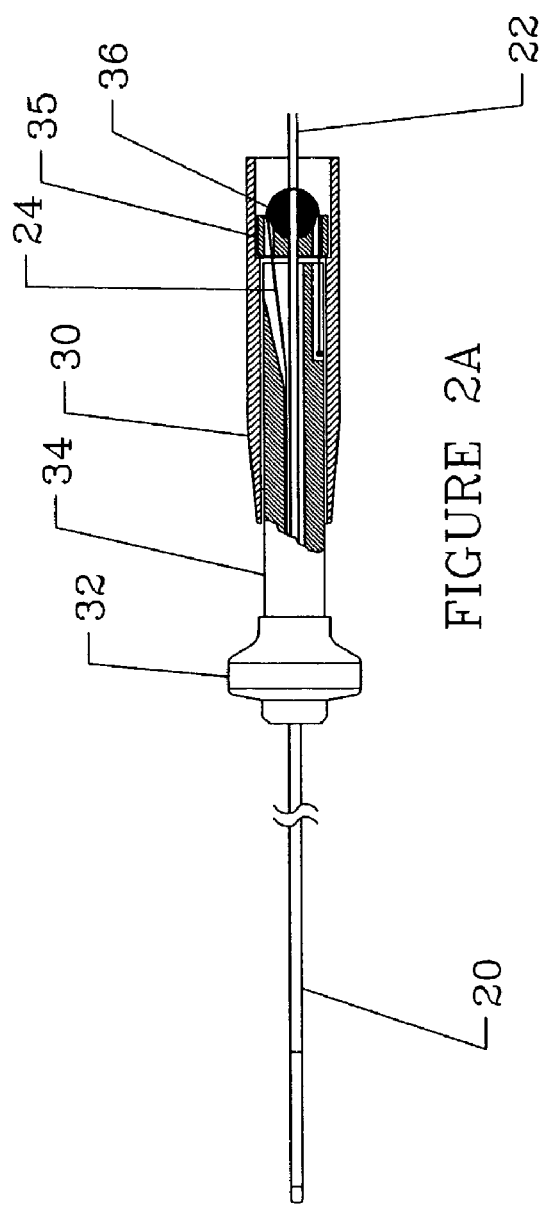
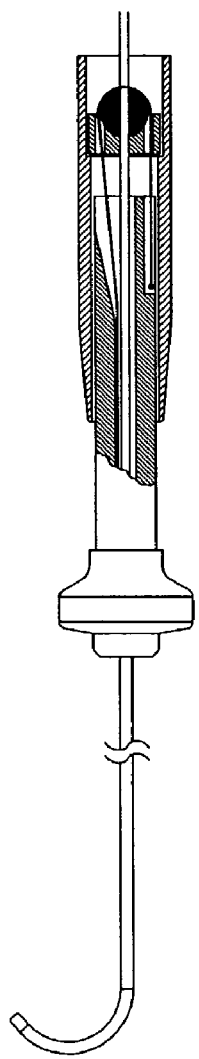
FIGURE 2A
FIGURE 2B

DEFLECTABLE MICROIMPLANT DELIVERY SYSTEM

BACKGROUND OF THE INVENTION

The present invention pertains to the field of catheter-based delivery systems. Particularly, it relates to an intravascular apparatus for delivering pharmacological or biological materials. More particularly, it involves a deflectable injection catheter for introducing therapeutic agents, such as cell cultures, growth factors, angiogenic agents, and the like, from within a chamber of the heart into damaged myocardium.

Coronary disease is the most prevalent cause of death in the United States. A heart attack, or myocardial infarction, occurs when coronary artery blockages severely restrict or deprive the heart muscle of blood flow. Blood supply which is greatly reduced or blocked for more than a transitory period of time can result in a significant loss of functioning heart muscle. The heart muscle cells, or cardiomyocytes, that die following a heart attack cannot be replaced by the body under normal conditions, because heart muscle cells are incapable of effective regeneration after injury or infarction. Instead, as a result of the healing phase after a heart attack, a scar is formed in the affected region of the heart.

This fibrous scar tissue cannot contract, does not contribute to heart function, and causes the rest of the heart to work harder and overcompensate for the nonfunctioning portion. As the uninjured regions of the heart become overburdened, a progressive deterioration can occur culminating in congestive heart failure.

Treatment options for damaged heart muscle and resulting end-stage heart failure include drug therapy, revascularization of the damaged tissue, mechanical circulatory assist devices, ventriculotomy, and heart transplantation.

Drug therapy is precluded in a number of refractory patients, generally only treat symptoms and has a limited effect on the progression of the disease. Transplant is limited by a shortage of donor hearts and need for continuous immunosupression.

Moreover, most of the above approaches involve highly invasive surgical procedures, with cardioplegic arrest and cardiopulmonary bypass.

What is needed is a method and means for delivering therapeutic agents to such patients in a minimally invasive procedure. More preferably, the need exists for percutaneous, localized delivery of therapeutic and pharmacological agents.

Catheter systems have been proposed for myocardial revascularization, via drilling or boring channels in the myocardium, such as by laser or needle, and, possibly, deposition of angiogenic substances within the channels created as an adjunct thereto. Such devices, however, raise performance and safety issues.

Specifically, precise control of the depth of the channel into the myocardium so as not to pierce the epicardium. More specifically, prior deflectable injection catheters exhibit shrinkage in the catheter shaft due to compression thereof when the catheter is deflected. This can change the relative position of the needle and the catheter shaft leading to inaccurate readings on the depth of needle insertion into the tissue to be treated.

Also, without a retraction default mechanism such prior catheter systems can cause injury to the endocardium from the instruments used to drill or bore the channels, or during advancement and delivery to the target location from these instruments. Further, a catheter capable of accessing more difficult areas of the heart is advantageous to achieving full benefit of the procedure. Additionally, minimal resistance to the flow of the agents or materials being deposited is desirable.

BRIEF SUMMARY OF THE INVENTION

The invention presents a system for delivery of therapeutic agents and/or cellular-based matter into body tissue. And, more specifically, a deflectable catheter-based method and apparatus for injecting such agents and materials directly into damaged or injured muscle tissue.

Accordingly, the present invention provides a catheter system for precise and controlled delivery of therapeutic agents and cellular materials to one or more sites in target body tissue. These agents and materials can be in aqueous form, microspheres suspended in solution, gels, pellets or any other media, whether in solid or fluid form, capable of delivery through the inner lumen of the catheter.

The delivery system includes a distal shaft, a proximal handle assembly and inner core member. The handle assembly has a mechanism for setting and limiting the depth of insertion of the inner core member or injection needle, a slide for moving the injection needle between retracted and extended positions, a return spring for biasing the inner core member to the retracted position. In a further preferred embodiment, a modified pulley mechanism is incorporated for compensating for catheter shaft compression when the catheter is deflected.

In its most specific form, it is a further object of the present invention to provide a catheter-based delivery system for assisting in the percutaneous delivery and controlled injection of myogenic cells (myoblasts, myotubes, young muscle fiber cells), angiogenic substances, growth factors, drugs and other therapeutic agents to a desired endoventricular treatment site. The system provides for multiple injections to a predetermined needle insertion depth with a single core needle that can be advanced and retracted from the tip of the catheter.

In a further aspect of the invention, the delivery system is designed to perform with an inner core member having a sufficiently large inner diameter to minimize resistance to the flow of media through the inner core member and so as not to subject the media being injected to high pressures.

In another aspect of the invention, the injected media can include a radiopaque material. This is especially useful in situations where multiple injections in a spaced apart pattern are contemplated. Although, however, a radiopaque marker can be used with single injections also.

Further features and advantages of the invention will become apparent from the following detailed description taken with the accompanying drawings.

BRIEF DESCRIPTION OF THE SEVERAL VIEWS OF THE DRAWINGS

The invention is illustrated in the drawings in which like reference numerals and characters designate the same or similar elements throughout the figures of which:

FIG. 1 depicts a general view of the entire deflectable microimplant-delivery system;

FIG. 1A is a view through cross section A—A of the distal working length of the catheter assembly;

FIG. 1B is a view through cross section B—B of the proximal working length of the catheter assembly;

FIG. 2A depicts a cross section view of the distal portion of the handle assembly with the distal working length of the catheter in a substantially non-deflected mode;

FIG. 2B depicts a cross section view of the distal portion of the handle assembly with the distal working length of the catheter in a deflected mode;

DETAILED DESCRIPTION OF THE INVENTION

Figure 3:
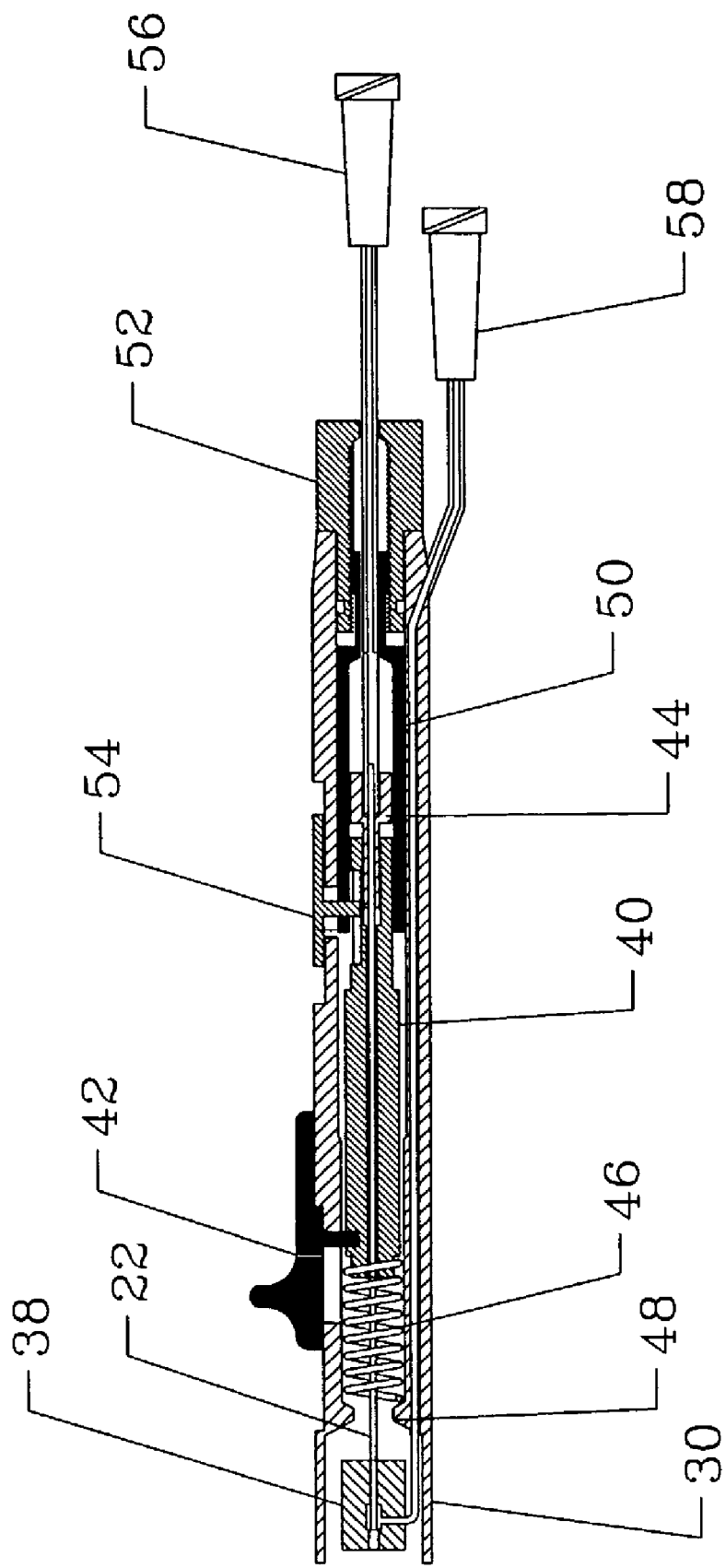
FIG. 3 shows a detailed cross section view of the proximal portion of the handle assembly.

The present invention relates to a deflectable catheter assembly including a distal shaft section, a proximal handle subassembly and an inner core member for delivery of therapeutic agents, cellular-based materials, or a combination thereof, to diseased, injured or defective tissue. The following description is presented to enable one of ordinary skill in the art to make and use the invention and is provided in the context of a patent application and its requirements. Various modifications to the embodiments described will be readily apparent to those skilled in the art and the generic principles herein may be applied to other embodiments. Thus, the present invention is not intended to be limited to the embodiments shown but is to be accorded the widest scope consistent with the principles and features described herein.

An overall view of the deflectable microimplant delivery system 10 is given in FIG. 1. This catheter apparatus includes shaft or working length (that portion of the catheter apparatus which physically enters the patient) 20 and handle assembly 30.

FIG. 1 also shows the deflection knob 32, inner core advancement control member 42, insertion depth gauge 54, inner core depth control knob 52, injection port 56 and sheath port 58, all of which will be explained in more detail below with reference to FIGS. 2A, 2B and 3.

FIG. 1A is a cross section through the distal portion of working length 20. This distal working length admits to an outer shaft with a multi-lumen section comprising a first inner lumen within which is the inner core member or needle assembly 22, a second lumen containing pull wire 24, which is fixed at its distal end to the distal portion of shaft 20, and a third lumen housing ribbon 26. When the pull wire 24 is tensioned, by distal advancement of the deflection knob 32, the distal end of the shaft 20 is deflected (as better seen in FIG. 2B).

In a preferred embodiment, ribbon 26 exists only in the distal portion of the shaft 20 as can be seen in a comparison between FIG. 1A and FIG. 1B (which is a cross section through the proximal portion of working length 20). The ribbon 26 assists in returning the distal tip of the catheter shaft to the substantially non-deflected position when deflection knob 32 is retracted proximally. Furthermore, ribbon 26 assists in the torquing and tracking of the distal portion of the working length 20 and in deflection thereof. The ribbon 26 also enhances pushability of the delivery system while maintaining integrity of the distal portion of the working length 20. Ribbon 26 can me made from any suitable material such as stainless steel, cobalt-chromium alloys, polymers and the like.

FIGS. 2A and 2B indicate the working length 20 of the catheter system along with a longitudinal cross section through the distal portion of the handle assembly 30. Pull wire 24 traverses a groove in pulley member 36 and is fixed at its proximal end to deflection rod 34. Pulley 36 is fixed to pulley base 35. In the embodiment shown, pulley base 35 is not fixed to the distal handle housing. But the pulley base 35 may be secured with respect to the handle assembly with, for example, mechanical fasteners, such as a set screw, or adhesives or the like.

When the deflection knob 32 is advanced distally, as shown in FIG. 2B, it places the pull wire 24 in tension, thereby causing the distal end of the shaft 20 to deflect. The pulley 36 is employed to substantially maintain the relative position of the inner core member 22 with respect to the distal end of shaft 20 when the shaft 20 is deflected (as better shown in FIG. 5). And pulley 36 also lessens the risk of the inner core member 22 from advancing out of, or retracting in from, the distal end of shaft 20 when the shaft 20 is manipulated during delivery to the site to be treated. Without the advantage of the pulley member 36, it has been found that, depending on the design of the handle assembly, the distal tip of the inner core member 22 can be caused to extend beyond, or retreat proximally, from the distal end of the shaft 20 unintentionally. And therefore, the relative position of the inner core member 22 with respect to the distal end of shaft 20 when the shaft 20 is deflected can vary leading to inaccurate insertion depths of the inner core member 22, without such advantage.

FIG. 3 shows the details of the proximal end of the handle assembly 30. This portion of the handle assembly 30 includes seal housing 38 surrounding the inner core member 22, slide member 40, insertion knob or inner core member advancement control 42, return spring 46, internal flange 48, depth stop member 50, depth knob or inner core insertion depth control 52, depth indicator or insertion depth gauge 54, injection port 56, and sheath port 58.

Insertion knob 42 is fixed to and slides with slide member 40. Slide member 40 can comprise a one piece unit or include a second proximal element 44 (as shown), for ease of manufacturing, which is fixed to the slide member 40 by, for example, mechanical fasteners, adhesives and the like. Insertion depth gauge 54, which is fixed to depth stop member 50, gives a visual indication of the maximum depth of insertion of inner core member 22. Inner core insertion depth control 52 sets the position of the insertion depth gauge 54. More specifically, rotation of depth knob 52, which threadingly engages depth stop 50, axially translates depth stop member 50 and depth indicator 54, therefore limiting maximum distal axial movement of inner core member 22 by limiting the maximum distal axial travel, in the embodiment shown, of second proximal slide element 44, which is fixed to the slide member 40, which is in turn fixed to insertion knob 42.

Injection port 56 is used to inject various therapeutic treatments such as myogenic cells, bone marrow derived stem cells, endothelial cells, cardiomyocytes, angiogenic growth factors, drugs or any combination thereof. Sheath port 58 is used to flush the lumen containing the inner core member 22.

In summary, the inner core insertion depth control 52 sets the maximum distance that the inner core member 22, slide member 40 and insertion knob 42 can travel. That maximum distance is indicated on the depth gauge 54. Inner core advancement control 42 is advanced manually against the bias of return spring 46. Return spring 46 has its distal end seated in abutting fashion to flange 48 formed on the inside of the handle assembly 30. The return spring 46 acts to retract the inner core member 22 when pressure is released on the insertion knob 42. When the inner core member 22 is advanced distally of the tip of shaft section 20 and into the desired treatment site, therapeutic agents can then be delivered through the injection port 56.

Figure 4:
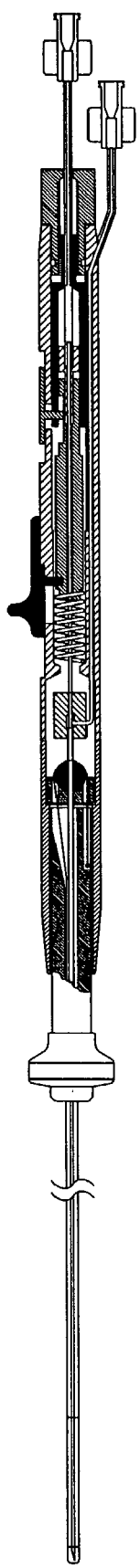
FIG. 4 is a cross section of the entire catheter assembly in a non-deflected position showing the relative position of the inner core member and the catheter.

FIG. 4 depicts a cut away view of the entire microimplant delivery system in the non-deflected mode with the inner core member in the retracted position.

Figure 5:
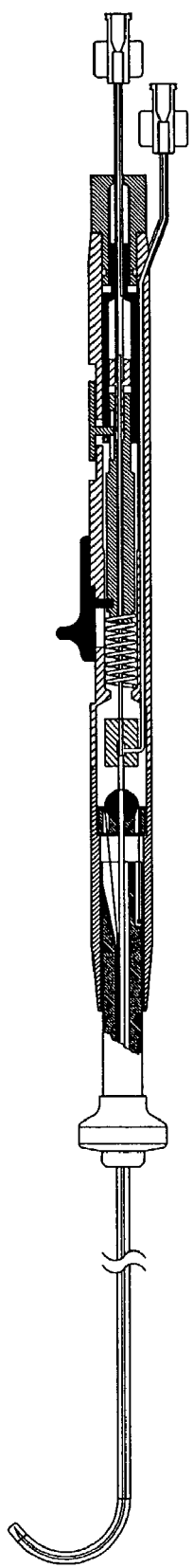
FIG. 5 is a cross section of the entire catheter assembly with the distal end in a deflected position indicating the relative position of the inner core member, with respect to the distal end of the catheter, remaining substantially unchanged.

FIG. 5 is similar to FIG. 4 except that the catheter apparatus is indicated in a deflected mode with the inner core member remaining in the retracted position.

Figure 6:
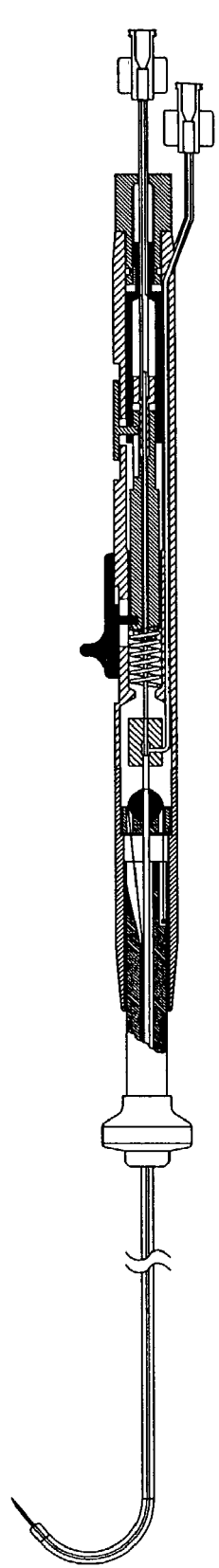
FIG. 6 is a cross section of the entire catheter assembly with the catheter shaft in a deflected position and the inner core member in an extended position.

FIG. 6 is a view similar to FIG. 5 except that the inner core member is now shown in an extended position.

By way of example, and not by way of limitation, the present invention is embodied in a deflectable microimplant delivery system 10 for treating regions of the myocardium damaged by myocardial infarction. In this embodiment, the system is introduced into the patient's vascular system through a major vessel in a manner and using techniques well known to those of ordinary skill in this art. With specific example to treating a regin or regions of the left ventricle, the system is introduced into the femoral artery, advanced up through the descending aorta, over the aortic arch, down the ascending aorta, through the aortic valve and into the left ventricle.

Using known imaging modalities, such as magnetic resonance, intracardic echocardiography, ultrasound, transesophogeal echocardiography, transthoracic echocardiography, fluoroscopy and the like, the location of the distal tip of the catheter shaft 20 within the left ventricle can be verified. Once manipulated to a region adjacent an infarct zone in the left ventricle, the catheter shaft 20 is deflected, by deflection knob 32, as depicted in FIG. 5, such that the distal tip is disposed against a site on the endocardial surface of the left ventricle. The maximum depth of insertion of the inner core member into the myocardium, if not having been previously set, is set via rotation of the insertion depth control knob 52. Inner core advancement control member 42 is then manipulated to move the inner core member 22 towards an extended position, as shown in FIG. 6, piercing through the endocardium and into the myocardium. In the embodiment shown in FIGS. 4–6, the inner core member 22 is provided with a beveled or skived tip to facilitate piercing of the endocardium through and into the myocardium. The desired therapeutic solution is then injected through the injection port and the inner core member into the myocardium. A number of injections may be performed at or around the infarct zone or the catheter can be repositioned to treat other areas of the left ventricle.

Other than the specific example given above, the deflectable microimplant delivery system described above can be used to inject therapeutic agents and cellular-based materials into any other chamber of the heart, such as by venous approach, for example femoral vein or internal jugular vein, or into almost any body tissue requiring treatment or repair. Including, for example, the kidneys, liver, brain, gastrointestinal tract, esophagus, and vascular system.

A deflectable catheter assembly with a working length section and a handle subassembly for delivery of one or more therapeutic agents and/or cellular-based therapies has been disclosed. Although the present invention has been described in accordance with the embodiments shown, one of ordinary skill in the art will readily recognize that there could be variations to the embodiments and those variations would be within the spirit and scope of the present invention.

For example, the inner core member and/or the distal portion of the catheter shaft could be designed to cause the inner core member to deflect at an angle oblique to the distal tip of the catheter shaft. This could allow for a longer track for the implanted media, with more therapeutic media being implanted with less risk of leakage of the therapeutic media. Moreover, this modification could also reduce the risk or likelihood of the inner core member piercing or passing completely through the organ or tissue to be treated.

Moreover, inner core member 22 can be drawn from a single piece of hypotubing or be formed as a multi-piece assembly. More specifically, needle assembly 22 can comprise a proximal hypotube portion, a distal skived hypotube section, with an intermediate polyimide tubing bonded at its proximal end to the proximal hypotube portin and at its distal end to the skived hypotube section. The latter described multi-section needle assembly enhances the overall deliverablity of the deflectable delivery system.

Additionally, the microimplant delivery system can be used to introduce a host of cellular matter to the treatment site, which can include myogenic cells, vascular endothelial growth factors, fibroblast growth factors, bone marrow derived stem cells, endothelial cells, cardiomyocytes or any combination of these or other biological or therapeutic agents.

Also, the catheter apparatus can be used as a tool for transmyocardial revascularization. In this manner the catheter apparatus, for example, could be used to form channels into the myocardium with or without the deposition of angiogenic enhancing substances such as vascular endothelial growth factors and fibroblast growth factors.

We claim:

1. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes means for limiting travel of the first member within said proximal section, said means for limiting travel housed within said proximal section, and said first member slideable with respect to said means for limiting travel; and wherein the means for limiting travel of the first member is secured to a depth indicator, said depth indicator providing a visual indication of the maximum travel of the inner member beyond the distal end of the distal section; and a third member mounted on the proximal section for moving the second member; and wherein said third member threadingly engages said second member such that rotational movement of said third member translates to lineal movement of said second member.

2. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes means for limiting travel of the first member within said proximal section, said means for limiting travel housed within said proximal section, and said first member slideable with respect to said means for limiting travel; and wherein the means for limiting travel of the first member is secured to a depth indicator, said depth indicator providing a visual indication of the maximum travel of the inner member beyond the distal end of the distal section; and wherein the depth indicator is capable of maintaining a visual indication of the maximum travel of the inner member beyond the distal end of the distal section when said inner member is in said extended position.

3. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes means for limiting travel of the first member within said proximal section, said means for limiting travel housed within said proximal section, and said first member slideable with respect to said means for limiting travel; and wherein the means for limiting travel of the first member is secured to a depth indicator, said depth indicator providing a visual indication of the maximum travel of the inner member beyond the distal end of the distal section; and means for deflecting the distal end of said distal section.

4. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes means for limiting travel of the first member within said proximal section, said means for limiting travel housed within said proximal section, and said first member slideable with respect to said means for limiting travel; and wherein the means for limiting travel of the first member is secured to a depth indicator, said depth indicator providing a visual indication of the maximum travel of the inner member beyond the distal end of the distal section; and insertion means fixed to and moveable with said first member for advancing said inner member to an extended position wherein the inner member extends beyond the distal end of the distal section.

5. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes means for limiting travel of the first member within said proximal section, said means for limiting travel housed within said proximal section, and said first member slideable with respect to said means for limiting travel; and wherein the means for limiting travel of the first member is secured to a depth indicator, said depth indicator providing a visual indication of the maximum travel of the inner member beyond the distal end of the distal section; and wherein the inner member extends through said distal section and said proximal section to a port at the proximal end of the proximal section.

6. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes means for limiting travel of the first member within said proximal section, said means for limiting travel housed within said proximal section, and said first member slideable with respect to said means for limiting travel; and wherein the means for limiting travel of the first member is secured to a depth indicator, said depth indicator providing a visual indication of the maximum travel of the inner member beyond the distal end of the distal section; and wherein the inner member is formed of hypotubing.

7. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes means for limiting travel of the first member within said proximal section, said means for limiting travel housed within said proximal section, and said first member slideable with respect to said means for limiting travel; and wherein the means for limiting travel of the first member is secured to a depth indicator, said depth indicator providing a visual indication of the maximum travel of the inner member beyond the distal end of the distal section; and wherein the inner member is a needle assembly comprising a distal skived hypotube, a proximal hypotube and an intermediate section of polyimide tubing bonded to the proximal and distal hypotubes.

8. A catheter system comprising:

a shaft section and a handle assembly, with said shaft section having a proximal end, connected to said handle assembly, and a distal end;

a needle assembly extending through said shaft section and into said handle assembly and capable of being advanced from a retracted position to an extended position wherein the needle assembly extends beyond the distal end of the shaft section;

said handle assembly housing a slide member slideable therein and a stop member slideable therein and slideable with respect to said slide member, said slide member being operatively joined to said needle assembly wherein movement of said slide member causes movement of said needle assembly between retracted and extended positions, said stop member being operatively associated with said slide member to limit the travel of said slide member;

means mounted in said handle assembly acting on said slide member to bias said slide member, and therefore said needle assembly to a retracted position; and wherein the stop member is secured to a depth indicator, said depth indicator providing a visual indication of the maximum travel of the needle assembly beyond the distal end of the shaft section.

9. The catheter system according to claim 8 wherein the means for biasing said slide member is a return spring.

10. The catheter system according to claim 9 wherein said return spring has two ends and said handle assembly further comprises an internal flange, wherein said return spring is positioned between said internal flange and said slide member in abutment against the internal flange on one end and the slide member on the other end.

11. The catheter system according to claim 9 further comprising a needle assembly advancement member, joined to said slide member and extending from said slide member to a position external of said handle assembly, for advancing said needle assembly from a retracted position to an extended position against the bias of the return spring.

12. The catheter system according to claim 8 further comprising means for deflecting the distal end of said shaft section.

13. The catheter system according to claim 8 wherein said handle assembly further comprises a deflection knob connected to the proximal end of the shaft section for deflecting the distal end of said shaft section.

14. A deflectable catheter assembly comprising:

a distal working length section and a proximal handle subassembly, said distal working length section having a proximal end, connected to said proximal handle subassembly, and a distal end, said proximal handle subassembly having a proximal end and a distal end;

means for manipulating said distal working length section between a substantially non-deflected position and a deflected position;

an inner core member, extending within the distal working length section and the handle subassembly;

means for manipulating said inner core member between a first position and a second position wherein said inner core member extends beyond the distal end of the distal working length section;

means for substantially maintaining the relative position of the inner core member and the distal end of the distal working length section when the distal working length section is manipulated between said substantially non-deflected position and said deflected position, said means for substantially maintaining the relative position housed within said proximal handle subassembly, and said inner core member slideable with respect to said means for maintaining the relative position; and wherein said means for substantially maintaining the relative position is secured to a depth indicator, said depth indicator providing a visual indication of the maximum travel of the inner core member beyond the distal end of the distal working length section.

15. The deflectable catheter assembly according to claim 14 wherein said means for manipulating said distal working length section between a substantially non-deflected position and a deflected position comprises a deflection rod having a deflection knob, wherein said deflection rod is slideable into and within the distal end of the handle subassembly and the deflection knob is connected to the proximal end of the distal working length.

16. The deflectable catheter assembly according to claim 15 further comprising a pull wire fixed to and extending from the distal end of the distal working length section to, and fixed to, the deflection rod.

17. The deflectable catheter assembly according to claim 14 further comprising a ribbon in the distal end of the distal working length section for assisting in returning the distal end of the distal working length section to a substantially non-deflected position.

18. The deflectable catheter assembly according to claim 14 wherein said means for manipulating said inner core member between said first position and said second position comprises a slide member slideable within said handle subassembly.

19. The deflectable catheter assembly according to claim 14 wherein the means for substantially maintaining the relative position of the inner core member and the distal end of the distal working length section, when the distal working length section is manipulated between said substantially non-deflected position and said deflected position, comprises a pulley.

20. The deflectable catheter assembly according to claim 16 wherein:

the means for substantially maintaining the relative position of the inner core member and the distal end of the distal working length section, when the distal working length section is manipulated between said substantially non-deflected position and said deflected position, comprises a pulley;

said pulley further comprising a groove, and said pull wire extends around said pulley within said groove to the position where it is fixed to said deflection rod.

21. The deflectable catheter assembly according to claim 20 wherein said pulley is fixed to a pulley base housed within said proximal handle subassembly.

22. A deflectable microimplant delivery system comprising:
a shaft having a proximal end and a distal end;
a handle assembly having a housing, a longitudinal axis, a depth control knob at a proximal end thereof and a deflection rod subassembly at a distal end thereof;
said deflection rod subassembly further comprising a deflection rod, and a deflection knob joined to the proximal end of the shaft for deflecting the distal end of said shaft from a first, substantially non-deflected position to a second, deflection position;
a hollow inner core extending within said shaft and said handle assembly and moveable from a first, retracted position and a second, extended position wherein said hollow inner core member extends beyond the distal end of said shaft;
a slide member and a depth stop member axially moveable within said handle assembly housing along said longitudinal axis, and said slide member being secured to said hollow inner core, said hollow inner core slideable with respect to said depth stop member;
said depth stop member further comprising a depth indicator acting to limit the travel of said slide member, said depth indicator providing a visual indication of the maximum travel of said hollow inner core member beyond the distal end of the shaft, and wherein manipulation of said depth control knob causes axial translation of said depth stop member along said longitudinal axis;
said slide member further comprising an insertion knob fixed to said slide member and extending to a point external of the handle assembly housing wherein manipulation of the insertion knob causes the hollow inner core to move between said first, retracted position and said second, extended position.

23. The deflectable microimplant delivery system according to claim 22 further comprising a spring mounted within the handle assembly housing for biasing said slide member proximally along said longitudinal axis and said hollow inner core to the second, retracted position.

24. The deflectable microimplant delivery system according to claim 22 further comprising a ribbon in the distal end of the shaft for assisting in returning the distal end of the shaft to a substantially non-deflected position.

25. The deflectable microimplant delivery system according to claim 22 further comprising:
a pulley subassembly; and
wherein the deflection rod assembly further comprises a pull wire, wherein the pull wire extends from the distal end of the shaft through the deflection knob and deflection rod and around said pulley subassembly to a point on the deflection rod where the pull wire is fixed to said deflection rod.

26. The deflectable microimplant delivery system according to claim 25, wherein said pulley subassembly comprises a pulley fixed to a pulley based.

27. The deflectable microimplant delivery system according to claim 26, wherein said pulley base is secured to said handle assembly housing.

28. A catheter assembly comprising:
a proximal section having a proximal end and a distal section having a distal end;
an inner member extending at least through said distal section and capable of being advanced from a first, retracted position to a second, extended position wherein the inner member extends beyond the distal end of the distal section;
said proximal section housing a first member and a second member therein, said first and second members are moveable with respect to each other within said proximal section, said inner member being secured to and moveable with said first member;
wherein said second member includes a stop member to limit travel of the first member within said proximal section, said stop member housed within said proximal section, and said first member slideable with respect to said stop member; and
wherein the stop member is secured to an inner member depth indicator; and
a third member mounted on the proximal section to move the second member; and
wherein said third member threadingly engages said second member such that rotational movement of said third member translates to lineal movement of said second member.

29. A catheter assembly comprising:
a proximal section having a proximal end and a distal section having a distal end;
an inner member extending at least through said distal section and capable of being advanced from a first, retracted position to a second, extended position wherein the inner member extends beyond the distal end of the distal section;
said proximal section housing a first member and a second member therein, said first and second members are moveable with respect to each other within said proximal section, said inner member being secured to and moveable with said first member;
wherein said second member includes a stop member to limit travel of the first member within said proximal section, said stop member housed within said proximal section, and said first member slideable with respect to said stop member;
wherein the stop member is secured to an inner member depth indicator; and
wherein the inner member depth indicator provides a visual indication of the maximum travel of the inner member beyond the distal end of the distal section when said inner member is in said extended position.

30. A catheter assembly comprising:
a proximal section having a proximal end and a distal section having a distal end;
an inner member extending at least through said distal section and capable of being advanced from a first, retracted position to a second, extended position wherein the inner member extends beyond the distal end of the distal section;
said proximal section housing a first member and a second member therein, said first and second members are moveable with respect to each other within said proximal section, said inner member being secured to and moveable with said first member;

wherein said second member includes a stop member to limit travel of the first member within said proximal section, said stop member housed within said proximal section, and said first member slideable with respect to said stop member; and wherein the stop member is secured to an inner member depth indicator; and wherein said proximal section comprises a deflection knob connected to said distal section to deflect the distal end of said distal section.

31. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes a stop member to limit travel of the first member within said proximal section, said stop member housed within said proximal section, and said first member slideable with respect to said stop member; and wherein the stop member is secured to an inner member depth indicator; and an advancement control member fixed to and moveable with said first member, said advancement control member to advance said inner member to an extended position wherein the inner member extends beyond the distal end of the distal section.

32. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes a stop member to limit travel of the first member within said proximal section, said stop member housed within said proximal section, and said first member slideable with respect to said stop member; and wherein the stop member is secured to an inner member depth indicator; and wherein the inner member extends through said distal section and said proximal section to a port at the proximal end of the proximal section.

33. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes a stop member to limit travel of the first member within said proximal section, said stop member housed within said proximal section, and said first member slideable with respect to said stop member; and wherein the stop member is secured to an inner member depth indicator; and wherein the inner member is formed of hypotubing.

34. A catheter assembly comprising:

a proximal section having a proximal end and a distal section having a distal end;

an inner member extending at least through said distal section and capable of being advanced from a first, retracted position to a second, extended position wherein the inner member extends beyond the distal end of the distal section;

said proximal section housing a first member and a second member therein, said first and second members are moveable with respect to each other within said proximal section, said inner member being secured to and moveable with said first member;

wherein said second member includes a stop member to limit travel of the first member within said proximal section, said stop member housed within said proximal section, and said first member slideable with respect to said stop member; and wherein the stop member is secured to an inner member depth indicator; and wherein the inner member is a needle assembly comprising a distal skived hypotube, a proximal hypotube and an intermediate section of polyimide tubing bonded to the proximal and distal hypotubes.

* * * * *